United States Patent
Gregersen et al.

(10) Patent No.: US 11,134,884 B2
(45) Date of Patent: Oct. 5, 2021

(54) APPARATUS FOR TESTING DISTAL COLONIC AND ANORECTAL FUNCTION

(71) Applicant: GI Bionics LLC, San Diego, CA (US)

(72) Inventors: Hans Gregersen, Ma On Shan (HK); Ghassan S. Kassab, La Jolla, CA (US)

(73) Assignee: GI Bionics LLC, San Diego, CA (US)

( * ) Notice: Subject to any disclaimer, the term of this patent is extended or adjusted under 35 U.S.C. 154(b) by 950 days.

(21) Appl. No.: 15/521,297

(22) PCT Filed: Oct. 21, 2015

(86) PCT No.: PCT/US2015/056777
§ 371 (c)(1),
(2) Date: Apr. 23, 2017

(87) PCT Pub. No.: WO2016/065082
PCT Pub. Date: Apr. 28, 2016

(65) Prior Publication Data
US 2017/0332958 A1    Nov. 23, 2017

Related U.S. Application Data

(60) Provisional application No. 62/243,051, filed on Oct. 17, 2015, provisional application No. 62/239,034, filed on Oct. 8, 2015.

(30) Foreign Application Priority Data

Oct. 22, 2014   (CN) .......................... 201420612247.4

(51) Int. Cl.
*A61B 5/00* (2006.01)
*A61B 5/03* (2006.01)
(Continued)

(52) U.S. Cl.
CPC ............ *A61B 5/4255* (2013.01); *A61B 1/041* (2013.01); *A61B 5/036* (2013.01); *A61B 5/0538* (2013.01);
(Continued)

(58) Field of Classification Search
CPC ... A61B 5/4255; A61B 5/6861; A61B 5/6873; A61B 5/036; A61B 5/1107
See application file for complete search history.

(56) References Cited

U.S. PATENT DOCUMENTS 6,584,348 B2    6/2003  Glukhovsky
7,787,926 B2 *  8/2010  Kimchy ............... A61B 6/4258
                                              600/407
(Continued)

OTHER PUBLICATIONS

Bharucha, Ae et al. "Anorectal disorders." Am. J Gastroenterol., Apr. 2010, vol. 105, No. 4, pp. 1-15.
(Continued)

*Primary Examiner* — Carrie R Dorna
(74) *Attorney, Agent, or Firm* — Reichel Stohry Dean LLP; Mark C. Reichel; Natalie J. Dean

(57) ABSTRACT

In at least one embodiment of a device configured for insertion into a gastrointestinal tract of the present disclosure, the device comprises a core comprising a core material which is solid, semi-solid or compressible, one or more sensors embedded in an interior of the device and/or on a surface of the device, at least one of the one or more sensors configured to obtain a pressure measurement within the gastrointestinal tract and during defecation of the device, and a plurality of electrodes within or upon the device and configured to obtain impedance planimetric measurements within the gastrointestinal tract and during defecation of the device, the impedance planimetric measurements useful to determine cross-sectional areas.

13 Claims, 9 Drawing Sheets

(51) Int. Cl.
  *A61B 5/0538* (2021.01)
  *A61B 5/11* (2006.01)
  *A61B 1/04* (2006.01)
  *A61B 5/06* (2006.01)
  *A61B 5/07* (2006.01)

(52) U.S. Cl.
  CPC .............. *A61B 5/065* (2013.01); *A61B 5/073* (2013.01); *A61B 5/1107* (2013.01); *A61B 5/6861* (2013.01); *A61B 5/6873* (2013.01); *A61B 2560/0468* (2013.01); *A61B 2562/0219* (2013.01); *A61B 2562/0247* (2013.01); *A61B 2562/0261* (2013.01); *A61B 2562/162* (2013.01)

(56) References Cited

U.S. PATENT DOCUMENTS

| | | | | |
|---|---|---|---|---|
| 7,970,455 | B2* | 6/2011 | Zilberstein | A61B 6/4258 600/436 |
| 2004/0230131 | A1* | 11/2004 | Kassab | A61B 5/1076 600/547 |
| 2008/0027358 | A1* | 1/2008 | Gregersen | A61B 5/036 600/593 |
| 2009/0118637 | A1 | 5/2009 | Kassab et al. | |
| 2010/0174271 | A1* | 7/2010 | Kassab | A61B 5/1076 604/540 |
| 2013/0158514 | A1* | 6/2013 | Elia | A61J 15/0076 604/516 |

OTHER PUBLICATIONS

Dall, Fh et al. "Biochemical wall properties of the human rectum—a study with impedance planimetry." Gut, Nov. 1993, vol. 34, No. 11, pp. 1581-1586.

Patent Cooperation Treaty (PCT), International Searching Authority, International Search Report, PCT/US2015/056777, dated March 29, 2016.

Patent Cooperation Treaty (PCT), International Searching Authority, Written Opinion of The International Searching Authority, PCT/US2015/056777, dated March 29, 2016.

* cited by examiner

APPARATUS FOR TESTING DISTAL COLONIC AND ANORECTAL FUNCTION

PRIORITY

The present application is related to, claims the priority benefit of, and is a U.S. 35 U.S.C. 371 national stage patent application of, International Patent Application Serial No. PCT/US15/56777, filed Oct. 21, 2015, which is related to, and claims the priority benefit of,, a) China patent application serial no. 2014 2 0612247.4, filed on Oct. 22, 2014, b) U.S. provisional patent application serial no. 62/239,034, filed on Oct. 8, 2015, and c) U.S. provisional patent application serial no. 62/243,051, filed on Oct. 17, 2015. The contents of each of the aforementioned patent applications are incorporated herein in their entirety.

BACKGROUND

The function of visceral organs like the gastrointestinal tract, the urinary tract and the heart or blood vessels is to a large degree mechanical. The following introduction refers mainly to the gastrointestinal tract but the invention relates to similar applications in other hollow organs such as the urinary tract and the biliary system in humans and animals.

The gastrointestinal tract is a long tube where ingested food is digested. Feces is formed from digested contents, from secretions and from micro-organisms in the distal part of the gastrointestinal tract. Muscle activity in the wall of the large intestine (so-called high amplitude propagated (contractile) sequences) pushes the fecal contents more distal and at some point when it reach the sigmoid colon, the person or animal feels urge to defecate, go to the restroom and expel the fecal contents as a voluntary action where the abdominal pressure is increased, the ano-rectal angle changes, and the anal sphincters relax. The biomechanical properties including the muscle contractile function and neural circuits (reflexes) are very important for this process.

The Specific Problem and Current Solutions.

The defecatory function is very complex which has two implications, 1) it is difficult to study the process in detail and 2) in many persons defecation is not functioning the way it should, for example many patients in China and Worldwide, especially elderly persons, suffer from constipation where they have difficulties to defecate. Whereas it is normal for most persons to defecate every day or every second day, constipated patients may only be able to do it once weekly or even more seldom.

Constipation can have many courses. For example it relates to hyposensitivity of nerve fibers or to lack of dietary fibers in the food. Since constipation and also other defecatory problems, such as pain during defecation, fecal incontinence, Hirschsprungs disease, extreme urge to defecate or diarrhea, are frequent diseases in the population, it is of great importance to measure and analyse data related to the defecatory process. Disordered defecation and incontinence are associated with significant economic and personal burdens. Our understanding of defecation is incomplete which at least in part rely on lack of appropriate investigatory tools.

Treatment of defecation problems rely on proper diagnosis. Treatments can be surgery, medical treatment or biofeedback. Defecation can be studied in specialized units in hospitals by means of several methods such as pressure recordings (manometry), balloon distension, endoscopy, ultrasonography, and radiographic examinations (defecography). Although these methods provide data on the function, they do not provide good measures of the forces the feces is exposed to and the resultant displacements. Most of the methods record only a few parameters and from one part of the system (for example only from the rectum or from the anal canal). Also symptoms usually do not correlate well to results from these tests and therefore the clinical value is limited. Other devices such as an ingestible capsule has been commercialised to measure the transit and pressures during passage from the esophagus to the anus. The commercialized capsule may record pressures and pH and may take photos throughout the passage of the gastrointestinal tract but it has limited use for evaluating defecatory function.

It will be an advantage with more advanced technology for diagnosing disordered defecation. Needless to say for clarifying mechanisms of dysfunction in patients such a device must make recordings during the passage from the sigmoid colon to the rectum and the anal canal. It should be as natural as possible, in other words imitate the normal feces and the defecation process, and provide measurements of forces, deformation, location and flow for detailed analysis of the process. The preferred embodiment of the present invention is an intraluminal solid or semisolid feces-like device with multiple sensors for analysis of the defecation process.

BRIEF SUMMARY

The invention consists of an electro-mechanical device that preferentially can be inserted into the rectum or colon for studying the mechanics of defecation. The device, in various embodiments, is semi-solid, bendable and compressible in order to have the same consistency as feces, and it contains a variety of sensors such as pressure sensors, force sensors, deformation sensors, gyroscopes, accelerometers and possible also imaging devices. It also contains energy supply for the electronic sensors. It may either contain means for storage of data or for wireless transmission of data to an external recording device. After insertion into the intestine, preferably in the sigmoid colon, the device can be expanded and decoupled from the insertion device. When the person being studied feels an urge to defecate, he or she will expel it. During this process the device can measure a variety of parameters such as pressure profiles, compression strain, bending, orientation, location, acceleration and flow, providing very detailed data on the defecation process. Detailed analysis of the data can be done by means of software programs. The distribution of signals, the shape of the device and position may be used to generate a graphical image of the passage of the device in the distal colon, rectum and anal canal.

In at least one embodiment of a device configured for insertion into a gastrointestinal tract of the present disclosure, the device comprises a core comprising a core material which is solid, semi-solid or compressible, one or more sensors embedded in an interior of the device and/or on a surface of the device, at least one of the one or more sensors configured to obtain a pressure measurement within the gastrointestinal tract and during defecation of the device, and a plurality of electrodes within or upon the device and configured to obtain impedance planimetric measurements within the gastrointestinal tract and during defecation of the device, the impedance planimetric measurements useful to determine cross-sectional areas.

In at least one embodiment of a device configured for insertion into a gastrointestinal tract of the present disclosure, the device further comprises a central support that stabilizes and supports the device while providing bending flexibility for the device to have comparable mechanical properties to normal feces.

In at least one embodiment of a device configured for insertion into a gastrointestinal tract of the present disclosure, the device further comprises an outer sizable structure comprising a bag or balloon around the core and configured to retain liquid or gas therein.

In at least one embodiment of a device configured for insertion into a gastrointestinal tract of the present disclosure, the central support is stiff or bendable. In at least one embodiment of a device configured for insertion into a gastrointestinal tract of the present disclosure, the core is compressible.

In at least one embodiment of a device configured for insertion into a gastrointestinal tract of the present disclosure, the central support, the core, or the outer sizable structure are at or between 3-10 cm long.

In at least one embodiment of a device configured for insertion into a gastrointestinal tract of the present disclosure, the device further comprises one or more additional sensors selected from the group consisting of force sensors, strain gauges, location sensors, gyroscopes, bending sensors, deformation sensors, accelerometers, and cameras.

In at least one embodiment of a device configured for insertion into a gastrointestinal tract of the present disclosure, the central support, the core, or the outer sizable structure are at or between 3-10 cm long, In at least one embodiment of a device configured for insertion into a gastrointestinal tract of the present disclosure, the device further comprises one or more additional sensors selected from the group consisting of pressure transducers, force sensors, strain gauges, location sensor, gyroscopes, bending sensors, deformation sensors, accelerometer, and miniature cameras for measurement of organ function.

In at least one embodiment of a device configured for insertion into a gastrointestinal tract of the present disclosure, the device further comprises an energy source.

In at least one embodiment of a device configured for insertion into a gastrointestinal tract of the present disclosure, the device further comprises a data storage unit.

In at least one embodiment of a device configured for insertion into a gastrointestinal tract of the present disclosure, the device further comprises a wireless transmission unit configured to communicate with an external receiver.

In at least one embodiment of a device configured for insertion into a gastrointestinal tract of the present disclosure, the device forms a system along with a display, a signal conditioning unit, and an analysis unit, wherein data obtained from the one or more sensors and/or the plurality of electrodes can be analyzed in terms of trajectories, force distributions, bending, angling, color contour plots, and/or 3D (three-dimensional) graphics, for transit function in an organ.

In at least one embodiment of a device configured for insertion into a gastrointestinal tract of the present disclosure, the device is configured for placement within the sigmoid colon or rectum and where the core material and the surface of the device have comparable properties to feces.

In at least one embodiment of a device configured for insertion into a gastrointestinal tract of the present disclosure, the device comprises a valve configured to connect to a tube, the tube used to provide the outer sizable structure with the liquid or the gas.

In at least one embodiment of a device configured for insertion into a gastrointestinal tract of the present disclosure, the device further comprises an attachment configured to permit an individual inserting the device into the gastrointestinal tract to push or pull the device to a preferred location.

In at least one embodiment of a device configured for insertion into a gastrointestinal tract of the present disclosure, the device is configured to be inserted into the gastrointestinal tract using an introducer that will be withdrawn from the device before operation of the device within the gastrointestinal tract.

In at least one embodiment of a device configured for insertion into a gastrointestinal tract of the present disclosure, the device comprises a long and narrow configuration.

In at least one embodiment of a device configured for insertion into a gastrointestinal tract of the present disclosure, the device further comprises one or more electrical stimulating sensors thereon, the one or more electrical stimulating sensors configured to deliver an electrical signal to a portion of the gastrointestinal tract.

In at least one embodiment of a device configured for insertion into a gastrointestinal tract of the present disclosure, the device further comprises a battery or energy source connected via wires to the one or more sensors and to the plurality of electrodes.

In at least one embodiment of a device configured for insertion into a gastrointestinal tract of the present disclosure, the device further comprises a stabilizing flexible or non-flexible core rod.

In at least one embodiment of a device configured for insertion into a gastrointestinal tract of the present disclosure, the device further comprises a stabilizing flexible or non-flexible core rod.

In at least one embodiment of a device configured for insertion into a gastrointestinal tract of the present disclosure, the battery or energy source is coupled to the stabilizing flexible or non-flexible core rod.

The present disclosure includes disclosure of use of any of the various device embodiments of the present disclosure.

In at least one use of an exemplary device of the present disclosure, the outer sizable structure can be inflated at different pressures and/or volumes and wherein diameters of the outer sizable structure can be recorded at the different pressures and/or volumes.

In at least one use of an exemplary device of the present disclosure, the diameters can be recorded as a circumference and a tension to produce a tension-length relation.

In at least one use of an exemplary device of the present disclosure, pressure measurements and impedance measurements can be obtained by the device within the gastrointestinal tract and during defecation of the device.

In at least one use of an exemplary device of the present disclosure, the pressure measurements and/or the impedance measurements obtained within the gastrointestinal tract and/or during defecation of the device can be used to diagnose a gastrointestinal condition.

In at least one use of an exemplary device of the present disclosure, a length (from circumference or diameter) and tension (from the product of pressure and diameter) can be determined using measurements obtained by the device.

BRIEF DESCRIPTION OF THE DRAWINGS

The disclosed embodiments and other features, advantages, and disclosures contained herein, and the matter of attaining them, will become apparent and the present disclosure will be better understood by reference to the following description of various exemplary embodiments of the present disclosure taken in conjunction with the accompanying drawings, wherein:

In FIG. 1A the device is shown in the sigmoid colon immediately after insertion. In FIG. 1B the device is passing down into the rectum and the anorectal angle is changed as it does during defecation. In FIG. 1C the device is about to be expelled through the anal canal. The elements as shown in these figures include 1: smart artificial pellet device (SAP), 2: anal sphincter, 3: rectum, 4: sigmoid colon, and 5: anorectal angle.

In FIG. 2A the artificial fecal pellet has a stabilizing flexible core in the interior which allows it to bend in different directions. In FIG. 2B an embodiment is shown without the central structure. FIG. 2C shows an embodiment with an outer balloon that can be inflated until the patient feel urge to defecate or experience other symptoms. FIG. 2D shows the connecting tube and an exemplary valve that is used during filling of the balloon. When the tube is disconnected, the valve secures that the fluid inside the balloon does not leak out. FIG. 2D also illustrates a loop structure at the tip which can be used for the doctor to drag the artificial fecal pellet with an endoscope up to the preferred location. The elements as shown in these figures include 6: central stabilizing flexible or non-flexible core rod, 7: pellet solid or semi-solid material, 8: sensors embedded in the interior of the artificial fecal pellet, 9: sensor on the surface or the artificial fecal pellet, 10: battery or energy source connected through wires to all sensors, transducers and transmitter, 11: data storage device or wireless transmitter to outside unit, 12: distensible shell like a balloon or bag that can be inflated, 13: liquid or gas inside the shell, 14: electrodes for impedance planimetric measurement of cross-sectional areas, 15: loop that the endoscope can attach to during insertion, 16: valve, and 17: tube for filling the outer structure such as a balloon.

In FIG. 5A the pellet further comprises one or more electrical stimulating sensors on the surface of the artificial fecal pellet. FIG. 5B shows an embodiment without a distensible shell like a balloon or bag that can be inflated, whereby the sensors embedded in the interior of the artificial fecal pellet, the battery, and the data storage device or wireless transmitter to outside unit are positioned on or within the central stabilizing flexible or non-flexible core rod. The elements as shown in these figures include 6: central stabilizing flexible or non-flexible core rod, 7: pellet solid or semi-solid material, 8: sensors embedded in the interior of the artificial fecal pellet, 9: sensor on the surface or the artificial fecal pellet, 10: battery or energy source connected through wires to all sensors, transducers and transmitter, 11: data storage device or wireless transmitter to outside unit, and 22: electrical stimulating sensor on the surface of the artificial fecal pellet.

In FIG. 6A the pellet further comprises at least one sensor configured as a camera and a light source, such as a flash, so to provide light so that the camera can obtain images within the patient. FIG. 6B shows an embodiment whereby the smart artificial pellet can make movements and thereby crawl in a direction within the body, such as up the colon, using a movement device and a motor. The elements as shown in these figures include 6: central stabilizing flexible or non-flexible core rod, 7: pellet solid or semi-solid material, 8: sensors embedded in the interior of the artificial fecal pellet, 9: sensor on the surface or the artificial fecal pellet, 10: battery or energy source connected through wires to all sensors, transducers and transmitter, 11: data storage device or wireless transmitter to outside unit, 23: sensor configured as a camera, 24: light source, such as a flash, 25: movement device, and 26: motor.

In FIG. 7A the pellet further comprises a bag or balloon positioned around the front and rear (proximal and distal) sensors configured as pressure transducers in order to measure a more reliable pressure during expulsion, such as shown in FIG. 1C. FIG. 7B shows an embodiment whereby certain components (the battery or energy source and the data storage device or wireless transmitter shown as exemplary components) are external to the pellet but connected to the pellet using thin wires. The elements as shown in these figures include 6: central stabilizing flexible or non-flexible core rod, 7: pellet solid or semi-solid material, 8: sensors embedded in the interior of the artificial fecal pellet, 9: sensor on the surface or the artificial fecal pellet, 10: battery or energy source connected through wires to all sensors, transducers and transmitter, 11: data storage device or wireless transmitter to outside unit, 27: bag or balloon positioned around a sensor; 28: liquid or gas inside the bag or balloon; and 29: wire.

In FIG. 8A the pellet further comprises an application-specific integrated circuit (ASIC) or printed circuit whereby one or more of the embedded sensor, the battery or energy source, the data storage device or wireless transmitter, and/or the electrodes for impedance measurements, are positioned thereon and/or otherwise coupled thereto. Such embodiments can comprise a processor configured to process the various types of data obtained using the various sensors and/or electrodes, and that data (processed and/or raw) can be stored within a storage medium, such as memory, of the device. FIG. 8B shows an embodiment whereby one or more magnets or magnetically-attractive elements can be used so to magnetically attach to an endoscope during insertion and/or to the tube for filling the outer structure such as a balloon. The elements as shown in these figures include 6: central stabilizing flexible or non-flexible core rod, 7: pellet solid or semi-solid material, 8: sensors embedded in the interior of the artificial fecal pellet, 9: sensor on the surface or the artificial fecal pellet, 10: battery or energy source connected through wires to all sensors, transducers and transmitter, 11: data storage device or wireless transmitter to outside unit, 12: distensible shell like a balloon or bag that can be inflated, 13: liquid or gas inside the shell, 14: electrodes for impedance planimetric measurement of cross-sectional areas, 16: valve, 17: tube for filling the outer structure such as a balloon, 30: application-specific integrated circuit or printed circuit, 31: processor, 32: storage medium; and 33: magnet or magnetically-attractive element.

Figure 1A:
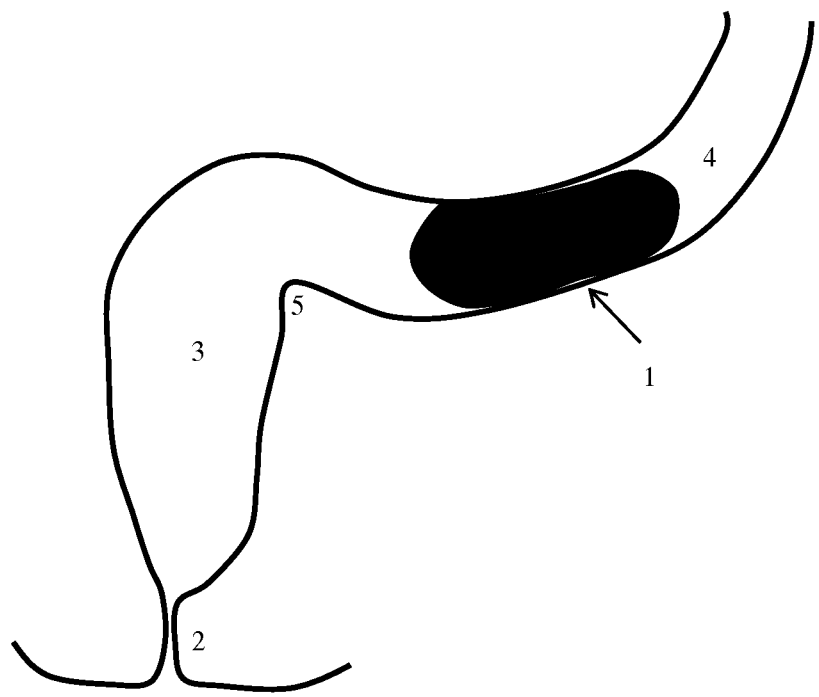
FIGS. 1A, 1B, and 1C: Sketches of the smart artificial pellet (an exemplary device or apparatus of the present disclosure) inside the intestine at different locations.

An overview of the features, functions and/or configurations of the components depicted in the various figures will now be presented. It should be appreciated that not all of the features of the components of the figures are necessarily described. Some of these non-discussed features, such as various couplers, etc., as well as discussed features are inherent from the figures themselves. Other non-discussed features may be inherent in component geometry and/or configuration.

DETAILED DESCRIPTION

For the purposes of promoting an understanding of the principles of the present disclosure, reference will now be made to the embodiments illustrated in the drawings, and specific language will be used to describe the same. It will nevertheless be understood that no limitation of the scope of this disclosure is thereby intended.

An object of the present disclosure is to record important physiological and pathophysiological parameters during defecation and to overcome disadvantages of conventional technologies. The various figures show several preferred embodiments of the invention. However, the shown embodiments in the figures are merely examples of embodiments. Other embodiments can be either more advanced or simplifications of the illustrated examples. Various embodiments of the invention include an electromechanical device to be inserted into a part of the gastrointestinal tract, preferable in the sigmoid colon with the purpose of recording parameters before and during defecation (in the remaining part of the document the electromechanical device is called smart artificial pellet or abbreviated SAP). The SAP consists in the preferred embodiment of one, two, or all of the following:

a) A central support that stabilizes and supports the whole device but yet provides the needed bending flexibility for the smart artificial pellet to have comparable mechanical properties to normal feces.

b) The core of the artificial fecal pellet where the core material can be solid or preferably semi-solid in order to make the pellet as physiological as possible. In other words, the SAP may be compressible and bendable as normal feces. Several electronic devices such as pressure sensors, force sensors, deformation sensors, accelerometers, gyroscopes, position sensors, miniature cameras and other devices can be embedded in the surface or in the interior of the core material for recording of relevant data variables such as position, velocity, acceleration, trajectory, pressure distribution, force and deformation. The list of sensors is not complete, basically the device can contain any sensor that is small enough to be embedded in the pellet. The core material or the central support may also contain an energy source like a battery and storage unit or wireless transmitter for data recorded by the sensors. The core material may be expandable and compressible according to which solution is best and the surface may be customized to obtain an optimal geometry and surface. For example, in an embodiment where the outer structure as mentioned below is not implemented, it will be preferable that the surface properties of the core imitate the surface properties of feces with respect to shear stress, viscosity and resistance to flow. Typically the core will be 2-10 cm long and 1-6 cm in diameter after insertion into the intestine but in some embodiments it may have other dimensions, both smaller or larger.

c) An outer sizable structure that in preferred embodiments is a bag embracing the core material and containing liquid or gas. In preferred embodiments the diameter of the structure after expansion is 3-10 cm in diameter but it may be smaller or larger in some embodiments. The purpose of expanding the structure is to create a size that is physiological after insertion and to create an urge to defecate. Needless to say the SAP may be smaller or larger and not necessarily spherical or elliptical, it can take any other preferred shape according to the design of the structure. The bag material may be customized to obtain an optimal geometry and surface. For example it will be preferable that the surface properties imitate the surface properties of feces with respect to shear stress, viscosity and resistance to flow.

In a preferred embodiment the SAP is 3-10 cm long, flexible in bending, and compressible in various directions in order to imitate normal feces. The device is comprised of a wireless intraluminal solid or semisolid bolus recording multiple signals such as pressures, forces, deformation, location, velocity acceleration, and direction. From one and up to several hundred sensors may be imbedded in the SAP to provide a detailed analysis of the defecation process, including geometry, location, and the forces the device is exposed to. The device can contain gyroscopes for data on the orientation, e.g. in both ends of the device to provide data on angling. The SAP may in preferred embodiments also contain sensors for tracking in a scanner or similar device. An exemplary embodiment is electromagnetic sensors that can be tracked to provide a trajectory of the path the bolus follows during the passage in the sigmoid colon and rectum during defecation. The displacement data together with the detailed distribution of surface parameters will provide multiple options for analysis of the system properties, e.g. color contour graphs of the bolus in relation to the displacement of it. The device will in preferred embodiments contain wireless data transmission units, memory for data storage, and energy source like a small battery.

Some sensors in the SAP may be force or deformation sensors based on strain gauge technology. They may also be based on measurement of electrical impedance in an impedance planimetric chamber system for measurement of cross-sectional area or diameter, or a system based on light (wave displacement or frequency). One solution is the use of pressure transducers embedded in the surface. The invention is however not restricted to the above solutions, i.e. they may be based on other technologies. It is noted that the electrodes used to obtain impedance measurements can include electrodes used to excite an electric field and electrodes (positioned within the excitation electrodes, namely the electrodes used to excite the field) used to detect the electric field so to obtain the impedance measurements, whereby said measurements can be used to determine cross-sectional area, diameters, and the like.

The sensors are connected with wires or wireless to one or more data acquisition systems that will amplify and condition the signals. Software (included within various hardware elements of the present disclosure, as appropriate, such as stored on a storage medium and accessed using a processor, on a data storage device, and/or included within various elements shown in FIG. 3) will be used for display and analysis, for example of color contour plots or other plots showing the passage of the device and the SAP geometry, and displacements/deformation. The data can be related to other recorded signals or to the stimulation magnitude imposed by various means.

The uniqueness of the invented SAP is that it has completely different purpose, structure and content than other known technologies for measurement inside the gastrointestinal tract. Technologies such as catheters with pressure sensors as used in high-resolution manometry and radiographic methods such as defecography are obviously very different. Ingestible capsules have been marketed with the purpose of measuring pressure and pH and for photographing the gastrointestinal tract from inside. Such capsules are however rather small and are not expandable and without sensors for measurement of force-deformation relations and these capsules do not provide detailed data on the defecation process.

Figure 1B:
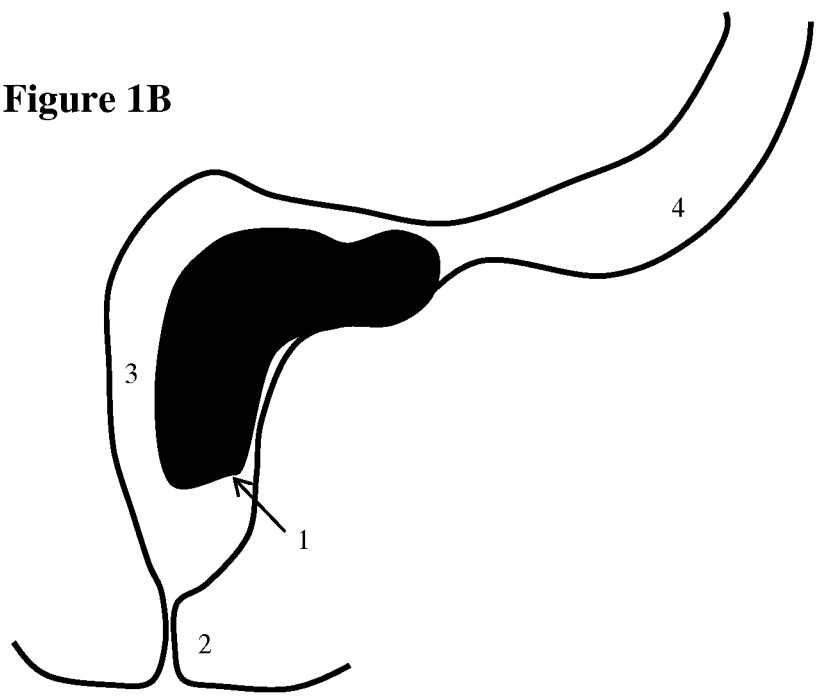
Figure 1C:
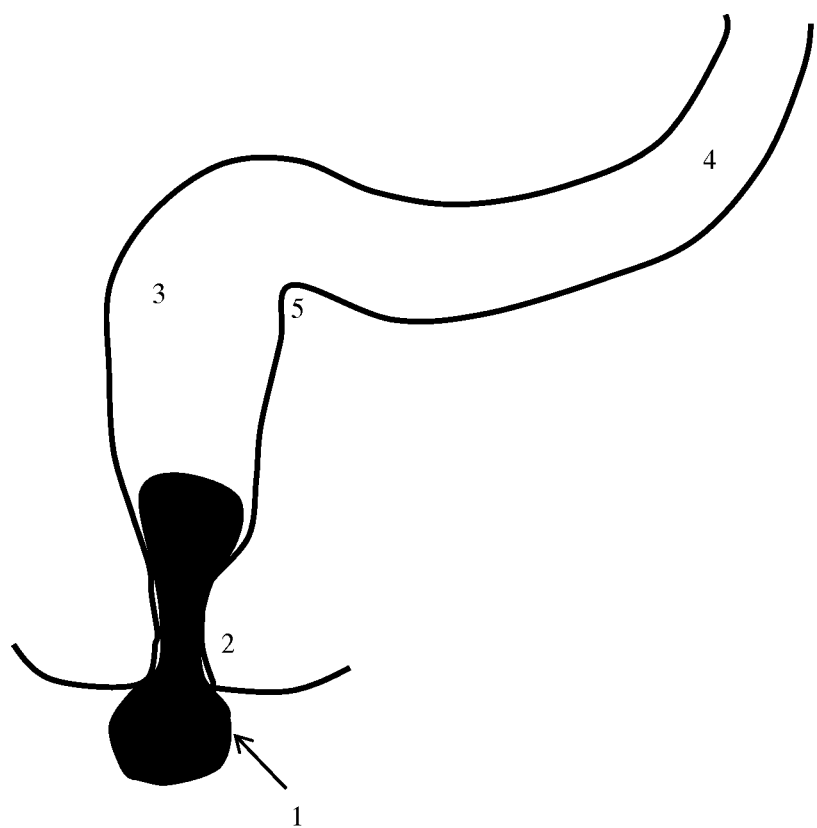
Figure 2A:
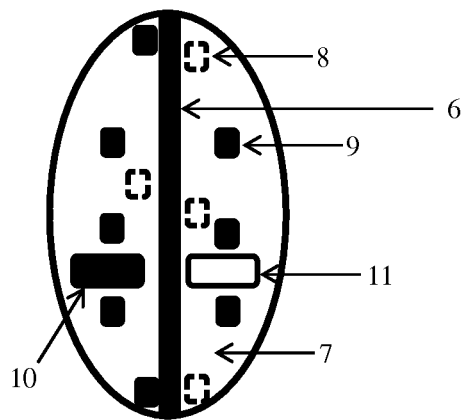
FIGS. 2A, 2B, 2C, and 2D: Sketches of different embodiments of the smart artificial pellet, in all of them various sensors are shown and other electronic components such as energy supply, memory unit, and transmitter.
Figure 2B:
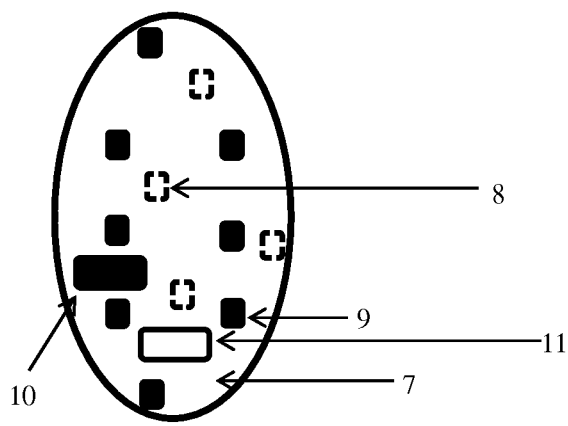
Figure 2C:
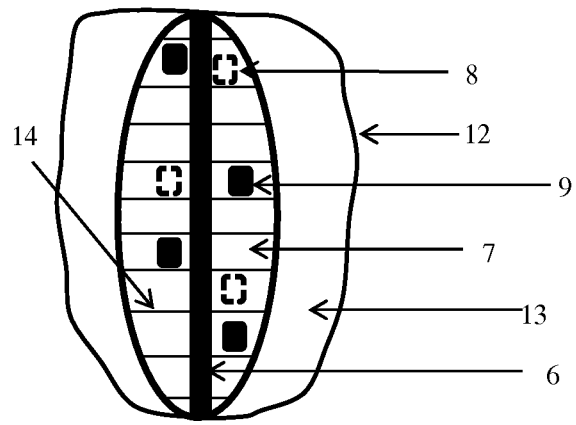
Figure 2D:
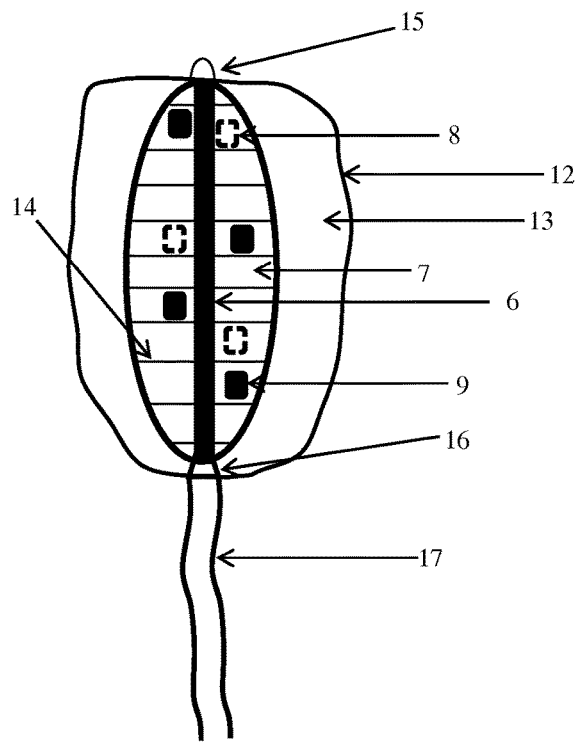
Figure 3:
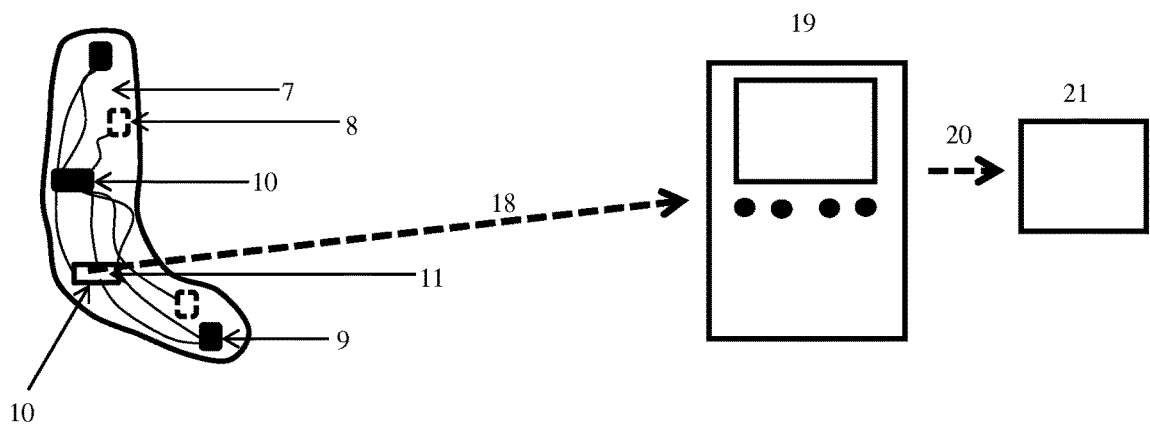
FIG. 3 shows a sketch of a system showing the smart artificial pellet, a receiver unit outside the body and a computer or other unit for storage, analysis and display of data. The elements as shown in this figure include 7: pellet solid or semi-solid material, 8: sensors embedded in the interior of the smart artificial pellet, 9: sensor on the surface or the smart artificial pellet, 10: battery or energy source connected through wires to all sensors, transducers and transmitter, 11: data storage device or wireless transmitter to outside unit, 18: wireless transmission to unit outside the body, 19: receiver unit with or without display; 20: wireless or wired transmission to computer or analysis unit, and 21: computer or analysis/graphics unit.
Figure 4:
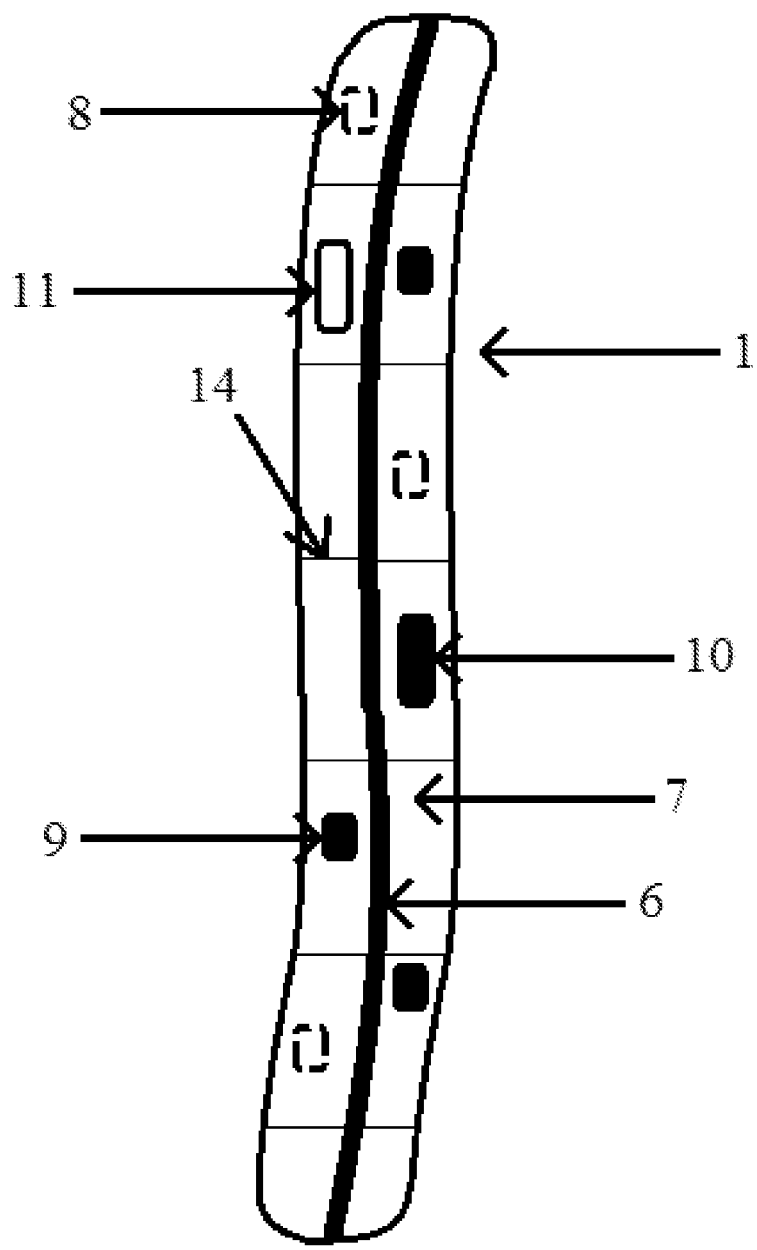
FIG. 4 shows an additional embodiment of the smart artificial pellet, having a relatively long and narrow "worm-like" configuration which can be swallowed by the patient or inserted by endoscope or surgery. The elements as shown in this figure include 1: smart artificial pellet device (SAP), 6: central stabilizing flexible or non-flexible core rod, 7: pellet solid or semi-solid material, 8: sensors embedded in the interior of the artificial fecal pellet, 9: sensor on the surface or the artificial fecal pellet, 10: battery or energy source connected through wires to all sensors, transducers and transmitter, 11: data storage device or wireless transmitter to outside unit, and 14: electrodes for impedance planimetric measurement of cross-sectional areas.
Figure 5A:
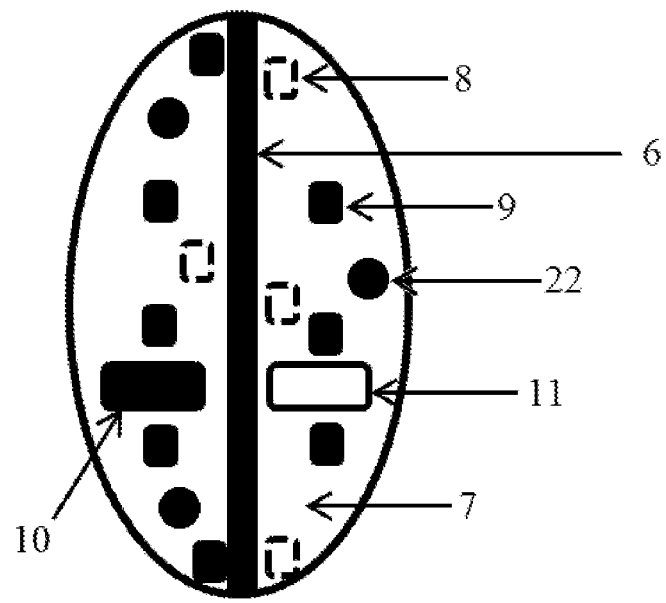
FIGS. 5A and 5B show different embodiments of the smart artificial pellet.
Figure 5B:
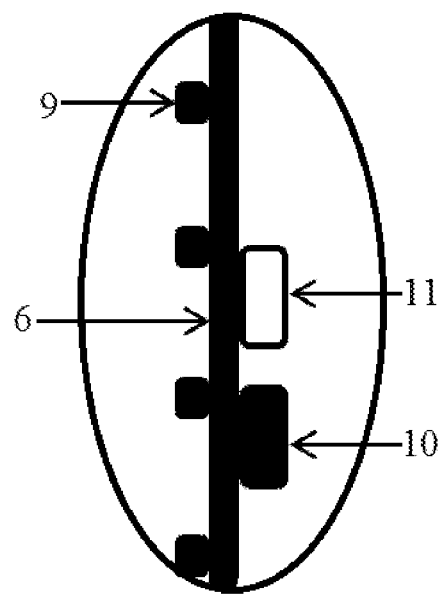
Figure 6A:
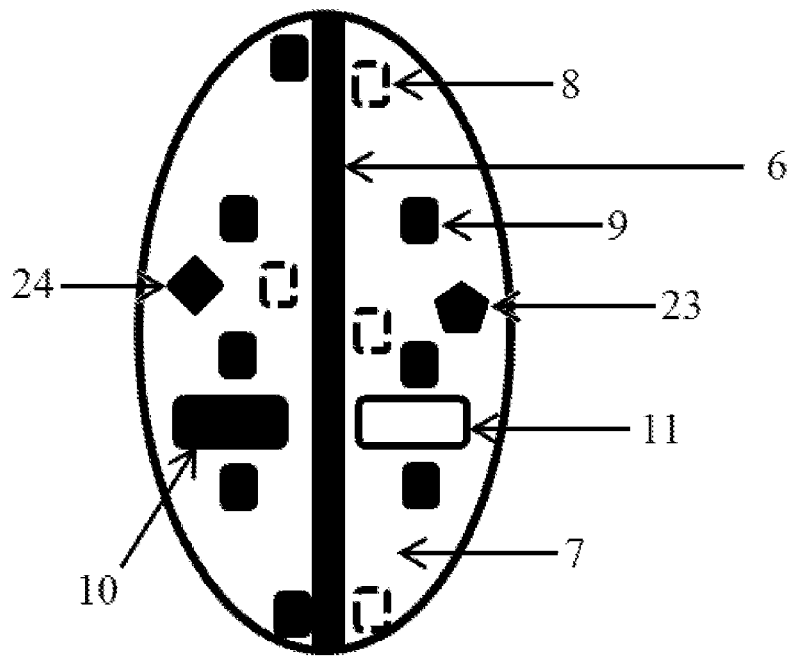
FIGS. 6A and 6B show different embodiments of the smart artificial pellet.
Figure 6B:
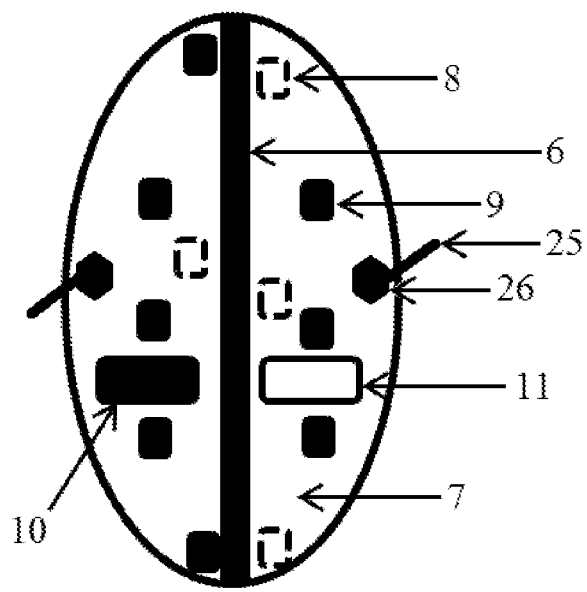
Figure 7A:
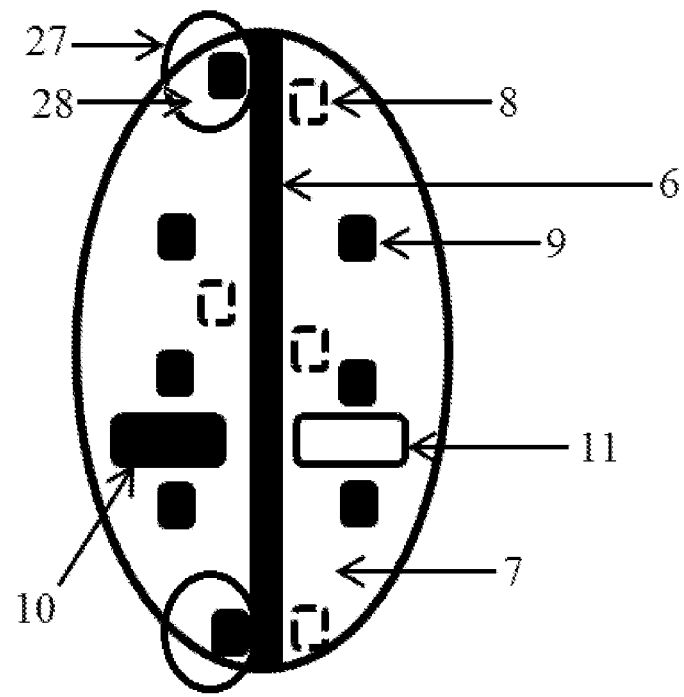
FIGS. 7A and 7B show different embodiments of the smart artificial pellet.
Figure 7B:
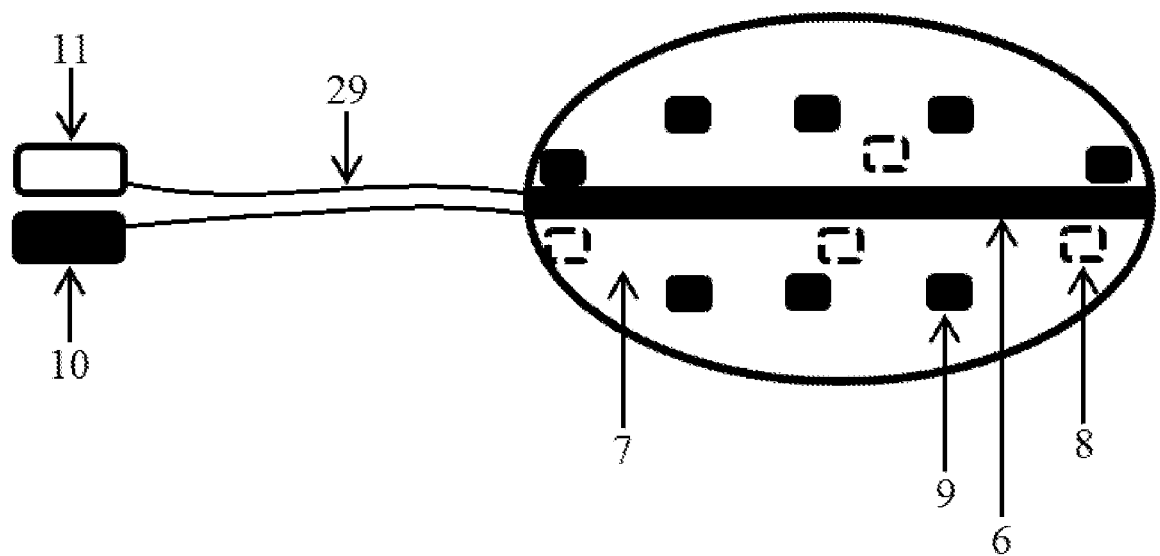
Figure 8A:
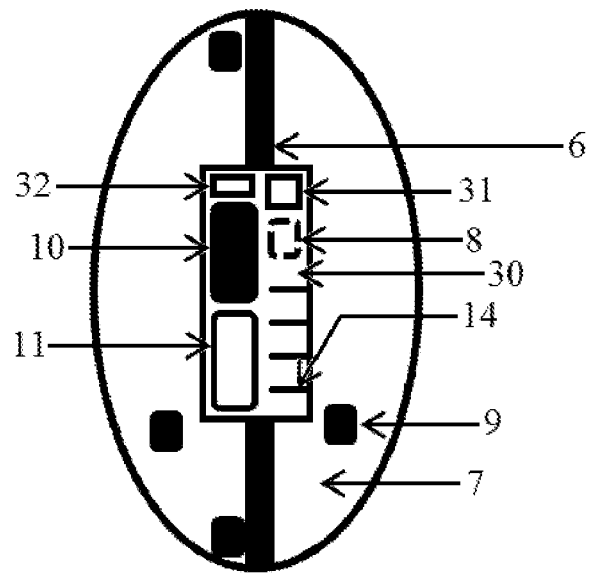
FIGS. 8A and 8B show different embodiments of the smart artificial pellet.
Figure 8B:
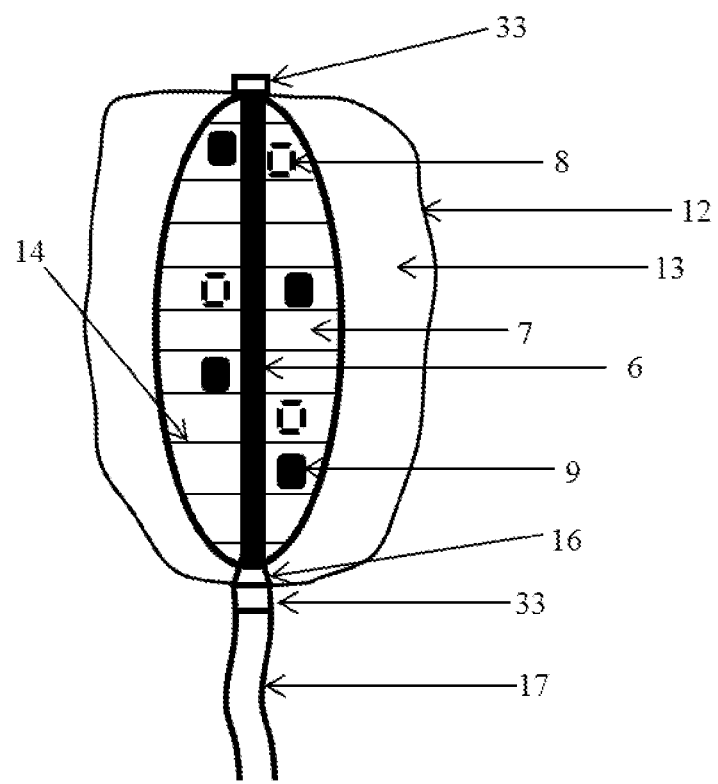

The preferred target organ is the sigmoid colon and rectum but it may apply to any part of the gastrointestinal tract and even to other organs. The device must be sized according to the size of the organ to be placed in. The abovementioned embodiments and figures are merely examples, i.e. the listing is not exclusive and many variants of the device may be produced, manufactured and commercialized. FIGS. 1-3 show several examples of embodiments. Various SAP embodiments can be used multiple times with multiple patients, whereby new sterile balloons or bags, such as shown in FIG. 2C, could be used prior to re-use of the device.

Additional embodiments of a SAP of the present disclosure can have a relatively long and narrow "worm-like" configuration which can be swallowed by the patient or inserted by endoscope or surgery. Such an embodiment can pass the entirety or part of the gastrointestinal tract. Such an embodiment may be the same or approximately the same length as other embodiments, or it may be longer, whereby the electrodes can obtain impedance data along a greater overall length of the SAP as may be desired.

Various SAP embodiments can also have one or more electrical stimulating sensors on the surface of the artificial fecal pellet. These electrical stimulating sensors can electrically stimulate (deliver an electrical signal to) portions of the gastrointestinal tract, such as the gastrointestinal wall and/or nearby nerves, such as the pudendal nerve close to the rectum, as pudendal nerve stimulation initiates the recto-anal inhibitory reflex. Additional SAP embodiments can operate without a distensible shell like a balloon or bag that can be inflated, whereby the sensors embedded in the interior of the artificial fecal pellet, the battery, and the data storage device or wireless transmitter to outside unit are positioned on or within the central stabilizing flexible or non-flexible core rod. Such embodiments can have a series of pressure sensors on the core to provide for high-resolution manometry during the passage of the device through the gastrointestinal tract.

Various SAP embodiments can further comprise at least one sensor configured as a camera and a light source, such as a flash, so to provide light so that the camera can obtain images within the patient. SAP embodiments can also be configured to make movements, and thereby crawl, through portions of the gastrointestinal tract, such as the colon, by itself. Furthermore, various embodiments can be used to obtain tension and/or strain data, by way of operation of sensors inside and/or on the surface of the SAP, which can be computed and viewed in real-time or offline. SAP embodiments can also be used to give a measure of the shear force or shear stress during movement of the SAP through the gastrointestinal tract.

SAP embodiments can also comprise a bag or balloon positioned around the front and rear (proximal and distal) sensors configured as pressure transducers in order to measure a more reliable pressure during expulsion. In various embodiments, certain components referenced herein can be external to the pellet but connected to the pellet using thin wires. Such components can be placed outside the anal canal and connected using the wires passing the anal canal to the device. Various components, such as the battery and/or wireless transmitter, can be on the outside and connected to the SAP using wires to save overall space within the device itself.

In various embodiments, the pellet further comprises an application-specific integrated circuit (ASIC) whereby one or more of the embedded sensor, the battery or energy source, the data storage device or wireless transmitter, and/or the electrodes for impedance measurements, are positioned thereon and/or otherwise coupled thereto. Various SAP embodiments can also have one or more magnets or magnetically-attractive elements can be used so to magnetically attach to an endoscope during insertion and/or to the tube for filling the outer structure such as a balloon.

Example of use of the invention. The physician in a specialized unit for defecatory disorders unpacks the device, make sure the battery is charged and that the SAP is functioning with recordings to an external device. The patient has beforehand been asked to empty the rectum for feces. The physician makes an endoscopy in the rectum and sigmoid and during that procedure the SAP is inserted and pushed or pulled up to the preferred location. The SAP can be expanded either by pulling it out from an embracing structure or by filling the bag until the patient feels urge to defecate. The physician disconnects the tube to the SAP and pulls it out. This leaves the SAP in the sigmoid colon without any connecting wires. The endoscope is slowly pulled out and the patient is allowed to defecate. Measurements are made by the device before and during defecation and the data may be visualized in real time by the receiver unit outside the person being studied. Detailed analysis may take place offline. Simultaneously the patient may record symptoms such as pain during the process. In case the patient cannot defecate the SAP, then it may be necessary to remove it in due time by endoscopy in a clinic or hospital. The physician or a technician will analyze the data and based on the analysis proper diagnosis and plan for treatment will be made. This is one exemplary use of a device of the present disclosure, noting that other uses (depending on device configuration and componentry) would be used as referenced herein.

The measurements referenced above (such as various mechanics and displacement) may also be dependent upon the diameter of the smart artificial pellet device (SAP) and/or the diameter or size of the inflatable balloon or bag. Each patient has a unique tension-length relation that can be determined by varying the diameter of the SAP and/or the balloon or bag and recording the corresponding tension (such as by way of pressure sensors). The tension-length relation can be calibrated for each patient to determine the appropriate diameter of the SAP and/or the balloon or bag used for that patient.

For example, the balloon or bag can be inflated at different pressures and/or volumes, and the diameter of the balloon or bag can be recorded as a circumference ($\pi \times$diameter) along with the tension (pressure$\times$diameter/2) to produce a tension-length relation. The resultant curve should be parabolic in shape, with the diameter corresponding to the ascending point of the curve selected for each patient. These objective measurements can compliment the subjective measurements referenced below.

Various cross-sectional areas or diameters, as referenced herein, can be determined by impedance planimetry. In many cases, the balloon or bag can be filled until the patient feels the urge or need to defecate (a subjective measurement), and then the tube used to fill the bag can be disconnected and the patient can then try to defecate the SAP. Tension and diameter measurements can be obtained during filling and during the defecation process, and the tension-length properties at various sensation levels, such as the urge to defecate that the pain threshold, can be obtained as well.

While various embodiments of devices and methods for using the same have been described in considerable detail herein, the embodiments are merely offered as non-limiting examples of the disclosure described herein. It will therefore be understood that various changes and modifications may be made, and equivalents may be substituted for elements thereof, without departing from the scope of the present disclosure. The present disclosure is not intended to be exhaustive or limiting with respect to the content thereof.

Further, in describing representative embodiments, the present disclosure may have presented a method and/or a process as a particular sequence of steps. However, to the extent that the method or process does not rely on the particular order of steps set forth therein, the method or process should not be limited to the particular sequence of steps described, as other sequences of steps may be possible. Therefore, the particular order of the steps disclosed herein should not be construed as limitations of the present disclosure. In addition, disclosure directed to a method and/or process should not be limited to the performance of their steps in the order written. Such sequences may be varied and still remain within the scope of the present disclosure.

The invention claimed is:

1. A device configured for insertion into a gastrointestinal tract, the device comprising:
    a core comprising a core material which is solid, semi-solid or compressible;
    a central support that stabilizes and supports the device while providing bending flexibility for the device to have comparable mechanical properties to normal feces, the central support disposed in the core and having a length extending only within the core;
    one or more sensors embedded in an interior of the device or on a surface of the device, at least one of the one or more sensors configured to obtain a pressure measurement within the gastrointestinal tract and during defecation of the device;
    a plurality of electrodes within or upon the device and configured to obtain impedance planimetric measurements within the gastrointestinal tract and during defecation of the device, the impedance planimetric measurements useful to determine cross-sectional areas; and
    an outer sizable structure comprising a bag or balloon around the core and containing a liquid or a gas therein, wherein the liquid or the gas is separate from the core material.

2. A device according to claim 1, wherein the central support is stiff or bendable.

3. A device according to claim 1, wherein the core is compressible.

4. A device according to claim 1, wherein the central support, the core, or the outer sizable structure are at or between 3-10 cm long.

5. A device according to claim 1, wherein the device further comprises one or more additional sensors selected from the group consisting of force sensors, strain gauges, location sensors, gyroscopes, bending sensors, deformation sensors, accelerometers, and cameras.

6. A device according to claim 1, wherein the device further comprises an energy source.

7. A device according to claim 6, wherein the device further comprises a data storage unit and a wireless transmission unit configured to communicate with an external receiver.

8. A device according to claim 1, forming a system along with a display, a signal conditioning unit, and an analysis unit, wherein data obtained from the one or more sensors or the plurality of electrodes can be analyzed in terms of trajectories, force distributions, bending, angling, color contour plots, or 3D graphics, for transit function in an organ.

9. A device according to claim 1, wherein the device is configured for placement within the sigmoid colon or rectum and where the core material and the surface of the device have comparable properties to feces.

10. A method of use of a device configured for insertion into a gastrointestinal tract, comprising the steps of:
    placing the device into a gastrointestinal tract, wherein the device comprises:
        a core comprising a core material which is solid, semi-solid or compressible,
        a central support that stabilizes and supports the device while providing bending flexibility for the device to have comparable mechanical properties to normal feces,
        an outer sizable structure comprising a bag or balloon around the core and containing a liquid or a gas therein, wherein the liquid or the gas is separate from the core material, and
        a tube for filling the outer sizable structure removably connected to the device;
    introducing the liquid or gas to inflate the outer sizable structure to a first pressure or a first volume via the tube;
    disconnecting the tube from the device; and
    recording a diameter of the outer sizable structure at the first pressure or the first volume.

11. The method of use of a device as in claim 10, further comprising the step of recording the diameter as a circumference and a tension to produce a tension-length relation.

12. The method of use of a device as in claim 10, further comprising the step of obtaining pressure measurements and impedance measurements within the gastrointestinal tract and during defecation of the device.

13. The method of use of a device as in claim 12, further comprising the step of diagnosing a gastrointestinal condition from the pressure measurements and the impedance measurements obtained within the gastrointestinal tract and during defecation of the device.

* * * * *